United States Patent
Morrow et al.

(10) Patent No.: US 6,589,489 B2
(45) Date of Patent: Jul. 8, 2003

(54) AIR PURIFIER

(75) Inventors: William H. Morrow, Barrie (CA); Larry James McLean, Barrie (CA)

(73) Assignee: L2B Environmental Systems Inc., Ontario (CA)

(*) Notice: Subject to any disclaimer, the term of this patent is extended or adjusted under 35 U.S.C. 154(b) by 65 days.

(21) Appl. No.: 09/822,886

(22) Filed: Mar. 30, 2001

(65) Prior Publication Data

US 2002/0168305 A1 Nov. 14, 2002

(51) Int. Cl.[7] .................................. B01J 19/08
(52) U.S. Cl. ...................... 422/186.3; 422/186.04; 422/121
(58) Field of Search ................... 422/186.3, 186.04, 422/186.07, 121

(56) References Cited

U.S. PATENT DOCUMENTS

| | | | | |
|---|---|---|---|---|
| 4,892,712 A | * | 1/1990 | Robertson et al. | 422/186.3 |
| 5,330,722 A | | 7/1994 | Pick et al. | 422/121 |
| 5,564,065 A | * | 10/1996 | Fleck et al. | 422/186.3 |
| 5,656,242 A | | 8/1997 | Morrow et al. | 422/121 |

FOREIGN PATENT DOCUMENTS

| | | |
|---|---|---|
| DE | 198 36 619 | 8/1999 |
| WO | WO 96/37281 | 11/1996 |

* cited by examiner

*Primary Examiner*—Kishor Mayekar
(74) *Attorney, Agent, or Firm*—Arnold B. Silverman; Eckert Seamans Cherin & Mellott, LLC

(57) ABSTRACT

An air purifier has an air flow path with a dielectric body interposed across the path. The dielectric body may be made of, for example, quartz or alumina fibers or silica granules or sponge so that it is porous to air and transmissive to ultraviolet ("UV") light. A source of ultraviolet light emits UV1 and UV2 light into the airflow path upstream of the dielectric body and at least UV2 light into the dielectric body itself. The UV light forms ozone. The ozone, as well as water vapor in the air, naturally attaches to the dielectric body which concentrates these materials in the dielectric body. The UV light irradiating the ozone and water in the dielectric body causes the formation of highly reactive hydroxyl radicals which assist in sterilizing the incoming air.

26 Claims, 3 Drawing Sheets

AIR PURIFIER

BACKGROUND OF THE INVENTION

This invention relates to an air purifier and to a method of air purification.

It is known that ultraviolet ("UV") light sterilizes DNA so that biological material (such as viruses, bacteria, molds, yeasts, and pollens) exposed to UV light either dies or cannot reproduce. This property of UV light has been utilized to sterilize air in a building by simply placing UV lamps in the building's air ducts. One drawback with this approach is that biological material may not be exposed to UV light for a sufficient time to be sterilized. To address this drawback, it is known to utilize a porous air filter and mount a UV light for reciprocating movement across a face of the filter. In operation, a fan draws air through the filter resulting in biological material becoming trapped in the filter. The irradiation of the filter with the reciprocating UV light acts to kill this trapped biological material. However some biological material, namely viruses, readily pass through porous filters and would not, therefore, be sterilized with the combination of a porous filter in conjunction with a UV lamp. Furthermore, UV light degrades a porous filter requiring frequent replacement of same.

In our U.S. Pat. No. 5,656,242 issued Aug. 12, 1997, we describe several air purifiers which sterilise air with UV radiation. In one embodiment air is drawn through a filter and a perforated metal plate into a primary radiation cavity containing a UV light. The filter traps biological material which is exposed to a low UV dose via the perforations in the metal plate. In another embodiment, air is drawn along a U-shaped path defined by a filter transmissive to UV2 and blocking UV1. UV1 and UV2 radiation generated by a lamp in the first leg of the U-shaped path forms sterilising ozone ($O_3$) in this leg; the UV2 which passes through the filter into the second leg of the U-shaped path breaks down this ozone. Water misters in this second leg result in the disassociated ozone forming hydroxyl radicals (OH) which further sterilise the air. Thus, the air is sterilised directly by the UV radiation and also indirectly by the UV radiation creating ozone and hydroxyl radicals. While this embodiment results in an effective purifier, water misters may not be readily available and increase maintenance needs of a system.

Therefore, there remains a need for an effective air purifier.

SUMMARY OF INVENTION

An air purifier has an air flow path with a dielectric body interposed across the path. The dielectric body is fabricated so as to be porous to air and transmissive to ultraviolet ("UV") light. A source of UV light emits UV light into the dielectric body and, optionally, also into the air flow path upstream of the dielectric body. The UV light may form ozone. Ozone, as well as water vapour in the air, naturally attaches to the dielectric body which concentrates these materials in the dielectric body. The UV light irradiating the ozone and water in the dielectric body causes the formation of highly reactive hydroxyl radicals which assist in sterilising the incoming air.

Accordingly, in one aspect, there is provided an air purifier comprising: an air flow path; a dielectric body which is porous to air and transmissive to ultraviolet light interposed across said air flow path; and a source of ultraviolet light for emitting ultraviolet light such that ultraviolet light is present in said dielectric body.

According to another aspect of the invention, there is provided an air purifier comprising: an air flow path; a dielectric body interposed across said air flow path, said dielectric body being porous to air and fabricated of at least one of silica, silicon dioxide, aluminum oxide, magnesium fluoride, calcium fluoride, barium fluoride, strontium fluoride, lithium fluoride, quartz and sapphire; and a source of ultraviolet light for emitting ultraviolet ("UV") light such that ultraviolet light is present in said dielectric body According to a further aspect of the present invention, there is provided a method of air purification comprising: passing contaminated air through a dielectric body which is porous to air and transmissive of ultraviolet ("UV") radiation; and UV irradiating said dielectric body.

BRIEF DESCRIPTION OF THE DRAWINGS

In the figures which illustrate example embodiments of the invention.

DETAILED DESCRIPTION OF THE PREFERRED EMBODIMENTS

Figure 1:
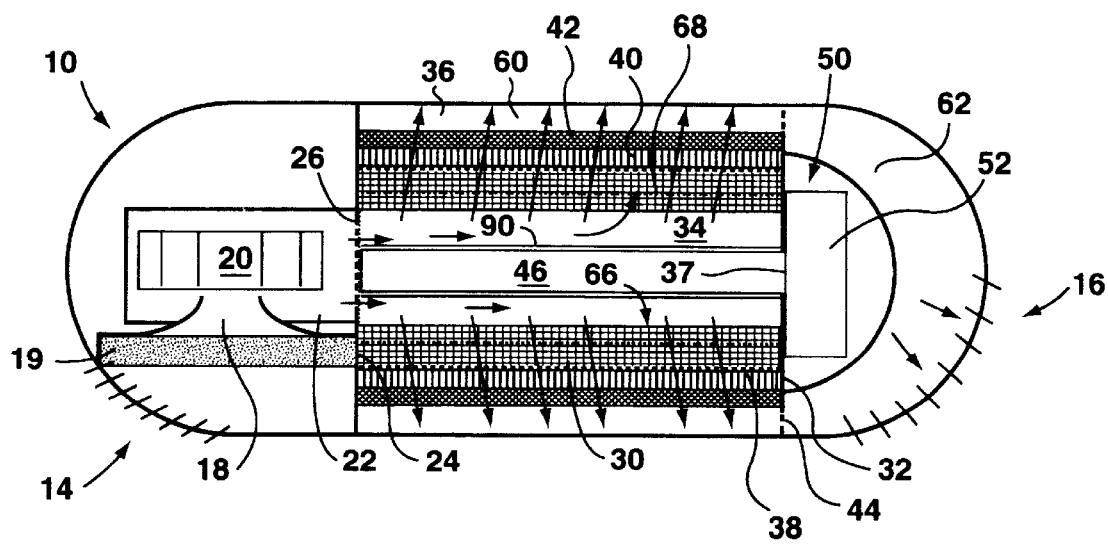
FIG. 1 is a schematic side view of an air purifier made in accordance with an embodiment of this invention.
Figure 2:
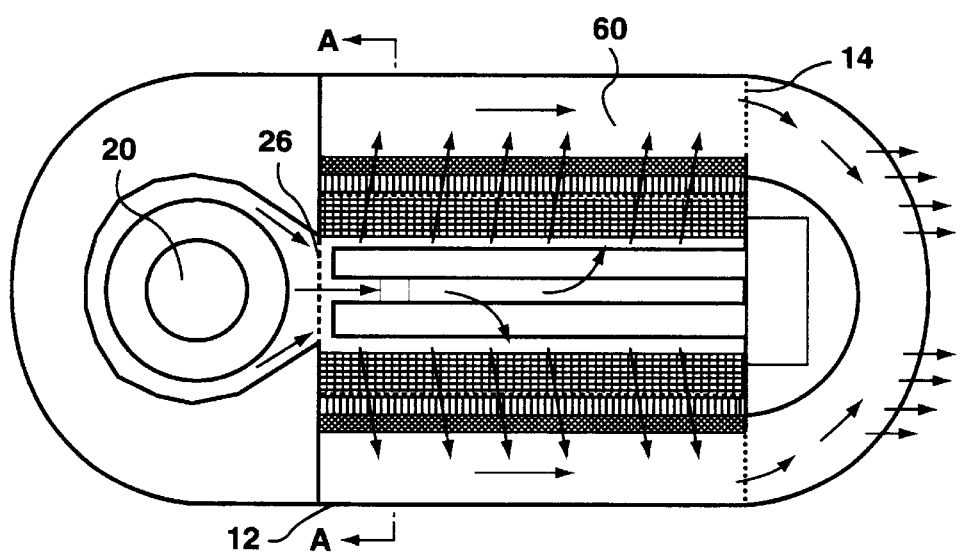
FIG. 2 is a schematic top view of the purifier of FIG. 1.
Figure 3:
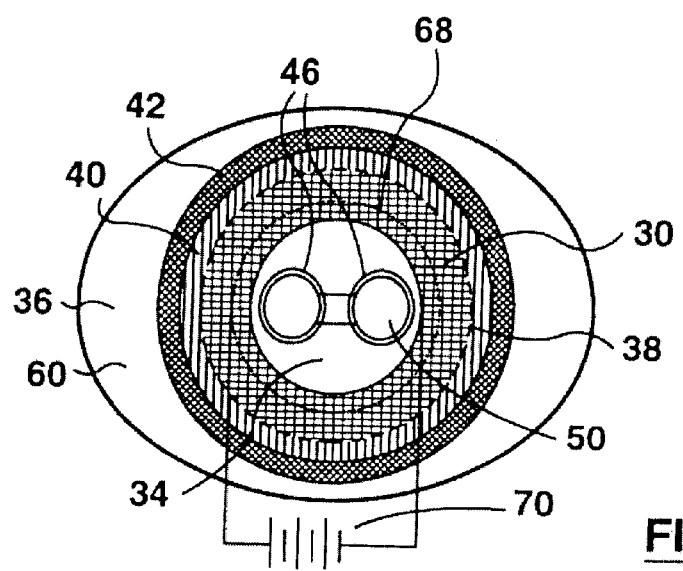
FIG. 3 is a schematic cross-sectional view along the lines 3—3 of FIG. 2.
Figure 3A:
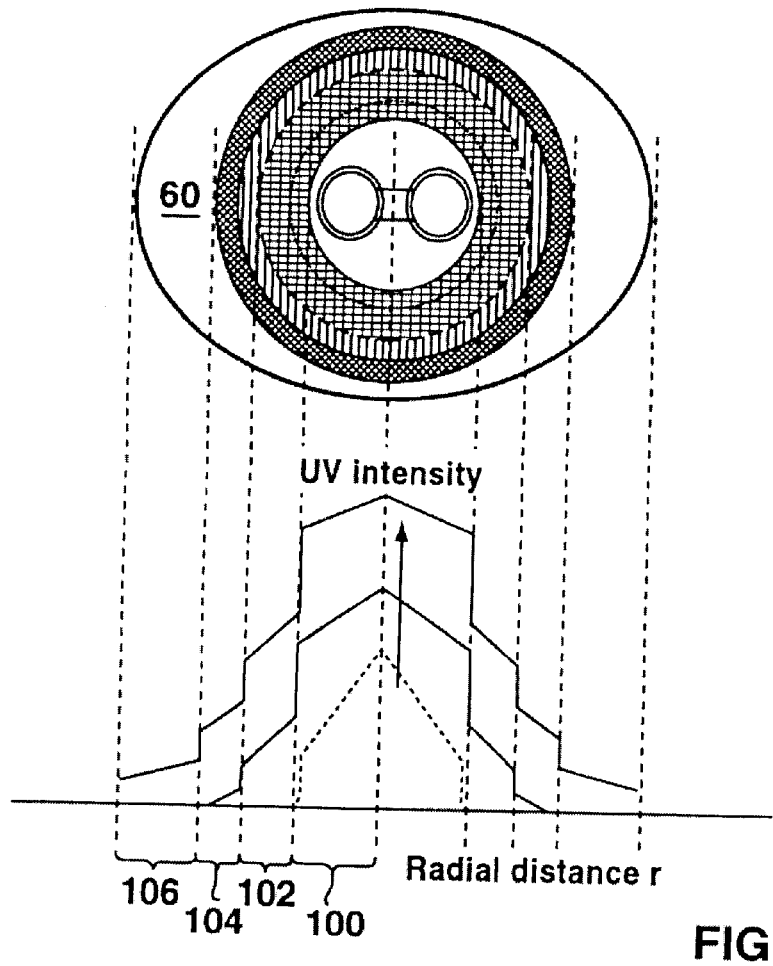
FIG. 3a is a graph of UV intensity versus radial distance.

Referencing FIGS. 1 to 3, an air purifier 10 has a housing 12 with an air intake 14 and an air exhaust 16. Within housing 12, an intake plenum 18 extends from the air intake 14, through a dust filter 19, to the suction inlet of a blower 20. An outlet plenum 22 extends between the outlet of the blower and an annular wall 24 inwardly depending from housing 12. Annular wall 24 has a concentric aperture covered with an ultra-violet ("UV") reflecting screen mesh 26 which allows the flow of air but which reflects UV. An annular dielectric body 30 extends between annular wall 24 and a second annular wall 32 inwardly depending from the housing to define a central cavity 34 and a peripheral annular cavity 36. Dielectric body 30 is enveloped by a screen mesh sleeve 38, a particulate filter 40, and a chemically absorbent filter 42. Sleeve 38 may, optionally, be provided with a UV coating on its inside surface such that it allows the transmission of air but reflects UV. The second annular wall 32 has a central opening 37 and a peripheral annular, UV reflecting, screen mesh section 44. The gas containing tube 46 of an ultraviolet lamp 50 extends through the opening 37 of wall 32 into cavity 34. The ballast 52 of lamp 50 is secured to wall 32.

Walls 24 and 32 along with the wall of the housing 12, define a UV chamber 60. The walls of this UV chamber many have a UV reflective coating. The outer cavity 36 opens into an exhaust plenum 62.

An inner member, shown as annular inner wire mesh 66, lines the inside wall of the dielectric body 30 and an outer member, shown as annular outer wire mesh 68 is embedded within the dielectric body 30. A voltage source 70 (FIG. 3) is connected (through a switch-not shown) between the inner mesh 66 and mesh sleeve 38, on the one hand, and outer wire mesh 68, on the other. Each mesh might be in the form of thin metal (Al with gold, rhodium or nickel coatings) radial blades which would reflect UV by grazing incidence but intercept significant amounts of light.

The intake and exhaust plenums 18 and 62 may be coated with a UV absorbing paint which, optionally, may be impregnated with a UV activated biocide such as $TiO_2$.

The UV lamp 50 may emit UV1, UV2 and UV3 radiation. UV1 radiation is defined as UV radiation below approximately 185 NM in wavelength, UV2 is defined as radiation between 185 and 300 NM in wavelength and UV3 is defined as UV radiation above 300 NM in wavelength.

UV1 radiation photo dissociates $O_2$ into ground state atomic oxygen (O) and water vapor into hydroxyl free radicals (OH) and hydrogen (H). UV2 radiation photo dissociates $O_3$ into $O_2$ and excited atomic oxygen (O*). These dissociation processes create powerful oxidants which can oxidize both bio-aerosols and volatile organic compounds rendering them either harmless, or converting them into species which are readily absorbed by filters. UV3 radiation does not photo dissociate any gaseous species but can excite photo catalysts, such as surfaces of $TiO_2$ and similar semiconductor catalysts.

All of these species will attach to surfaces in the annular dielectric 30 resulting in a concentration of the processes of oxidation. In this regard, when voltage source 70 is switched in, photo-electrically generated electrons from the inner wire mesh 66 and mesh sleeve 38 flow towards the oppositely charged outer mesh 68. These electrons attach to particulate and to the outer wire mesh 68. Such charge attachments retard the flow of the particulate enhancing the UV exposure by increasing the exposure time. In addition, electrostatic attachment of the particulate to the outer filters is enhanced increasing the efficiency of the filtration of the particulate.

The photoelectric effect is enhanced at shorter wavelengths for many materials. Thus using the inner wire mesh 66 as the cathode, which is near the lamp, would allow UV1 to be used to eject photo-electrons. An alternate method to using a mesh would be to coat a thin metal transparent conductive film directly on the lamp. Such cathodes (usually called semitransparent) are commonly used in optical sensing devices. This cathode should absorb only a tiny amount of UV1 exiting the lamp but could be highly photo-emissive by virtue of the enhanced quantum efficiency at shorter wavelengths. A very thin layer of gold, nickel, rhodium or other metal might be used. Cesium iodide or cesium telluride (in small quantity or low concentration) might also be used.

The inner mesh cathode 66 of the dielectric body may be coated with a UV reflective coating or may be constructed with a UV reflective material such as aluminum or aluminum coated with rhodium. This would concentrate the UV1 and UV2 in the central cavity 34 increasing the kill of bio-aerosols and photo-dissociative effects in the air. In addition, UV enhancement in the central chamber will not be at the expense of UV reaching the dielectric body if the reflective coating has a low absorbance. This occurs since the intensity of light inside the central cavity 34 will increase proportionately to the reflectance of the inner mesh cathode 66. Even though the cathode will transmit a smaller percentage of the light striking it, a larger amount of light will be available at its surface. Thus, a higher intensity of UV can be gained inside the central cavity 34 while preserving the flux into the annular dielectric body 30.

The UV reflective coating of the UV chamber 60, the inner mesh cathode 66, and the screen mesh sleeve 38 may be comprised of rhodium coated aluminum which can exhibit both high reflectance and a photoelectric effect. It may also be pure aluminum with a very thin protective film to protect it from oxidation but which will allow photoelectrons to escape. Such a film might be comprised of pure aluminum oxide, magnesium fluoride, or other fluoride material. The coating might also be comprised of an alkali metal with high UV reflectance in pure form and high photoelectric effect with a thin oxidation protective film such as a fluoride. The mesh size of the screen mesh sleeve 38 is chosen so that the preponderance of UV light reaching the sleeve is reflected. One way of achieving this is to keep the mesh size less than one tenth the size of the smallest wavelength to be reflected in a conductive mesh. In this fashion the mesh could serve as a particulate filter as well as a light reflector.

Unlike UV2 and UV3, UV1 radiation forms ozone which is a toxic gas. Consequently, it is desirable that most, or all, of the UV1 radiation be absorbed within central cavity 34 so as to reduce the prospect of ozone leaking from purifier 10.

The radial extent of the central cavity 34 of UV chamber 60 may therefore be dependent on the largest wavelength of UV1 produced by lamp 50. More particularly, in some embodiments of the invention, it may be desirable to have the most of the UV1 at no greater than 170 NM. In such instance, even with the radial extent of the inner cavity being on the order of a few mm, most of the UV1 radiation will be absorbed by the air of the inner cavity 34. On the other hand, if the lamp produces UV1 at up to 185 NM, the radial extent of the inner cavity would need to be on the order of at least 10 cm for most of this radiation to be absorbed while traversing the inner cavity.

The dielectric body 30 is formed so as to be porous to air. Consequently, an air flow path is defined from purifier air intake 14, through the blower 20, into the central cavity 34 of the UV chamber 60, then through the annular dielectric body 30, the screen mesh sleeve 38, outer particulate filter 40, outer chemically absorbent filter 42, into the outer cavity 36 and out the air exhaust 16.

The dielectric body 30 is fabricated of a porous dielectric material which transmits UV radiation. Suitable materials could include:

1. Silicon dioxide or pure silica in the form of fiber, sponge or frit
2. Silicon dioxide or pure silica in the form of an aerogel or xerogel
3. Silica gel granules
4. Silica gel granules coated onto silicon dioxide fibers or frit
5. Aluminum oxide (high purity) fibers, frit or granules
6. Aluminum oxide (high purity) coated aluminum fiber
7. Magnesium fluoride, calcium fluoride, barium fluoride, strontium fluoride or lithium fluoride powers, fibers, frits or coatings on transmitting or reflecting substrates.
8. Quartz fiber, quartz fiber with silica gel coating.
9. Sapphire fiber.

Other dielectric matrices with air passageways may also be used. Two properties are, however, needed: that the dielectric body transmit UV (UV1, UV2 and UV3) and that ozone and water vapour attach to the dielectric body. The latter property increases the availability of these species for photo-catalytic reactions which convert UV light into hydroxyl free radicals.

Water vapour and ozone will attach (i.e., bond) to all dielectrics to at least some extent. However, in some dielectric materials this property is particularly pronounced. For example it is well known that silica gel can absorb up to 30% of its mass of water vapor and ozone. For any dielectric material, the ability to attach to ozone and water vapour will increase if the material is provided with a large surface area.

This suggests that the porous dielectric body should have relatively small pores to increase surface area (limited only in that the pores should not be so small as to inhibit the admission of the molecules of water and ozone).

Optionally, the dielectric body is fabricated of a material which more strongly absorbs UV1 radiation than it does UV2 radiation. This may be desirable where the radial extent of the inner cavity is such that an appreciable portion of the UV1 radiation is not absorbed in the air of the central cavity 34. One suitable dielectric material with this property is quartz which, depending on the grade, will absorb more strongly at wavelengths below 185 nm than for wavelengths above 185 nm. Another material which may be suitable is aluminum oxide, provided it has sufficiently high purity to transmit UV.

The outer particulate filter 40 may be a pleated fabric filter or a fiber filter, which will trap biological contaminants such as virus, bacteria and moulds. UV light that transmits through the screen mesh sleeve 38 will sterilize the biological material on the filter. The outer chemically absorbent filter 42 may be a charcoal or zeolite filter, both of which will trap gaseous chemical contaminants as well as biological material. The life of outer filter 42 will be enhanced if it is placed after (in the air flow sense) the particulate filter. This will insure that its absorbent material pores do not clog with micro particles. Filter 42 will serve to remove any residual organic breakdown fragments from the photochemical reactions that oxidize volatile organic compounds in the dielectric body 30 insuring the safety of the device.

Since UV2 and UV3 are expected to penetrate into the two outer filters 40, 42, photocatalytic materials such as $TiO_2$ may be added to either or both of these filters. This will produce a continuous cleaning effect, which may serve to cleanse the filters of organic particulate material, enhancing their lifetimes. The dielectric body 30 will also produce hydroxyl free radicals in the gas phase which will be entrained in the gas flow and which will also serve to continuously clean the filters of particulate. The dielectric body may also be coated with a photocatalytic material such as $TiO_2$ to enhance the destruction of volatile organic compounds.

Since UV3 will be readily transmitted through many materials, it is expected to make its way through the outer filter 42 and into the outer cavity 36. The outer wall of housing 12, which can also be coated with photo catalytic material, can then absorb UV3. Since the appropriate concentration of this material will act as a strong UV absorber, the outer wall will both absorb residual UV and add to the overall volatile organic compound removal by the device.

In operation, both the blower 20 and UV lamp 50 are activated and the switch to voltage source 70 is closed. The voltage then polarizes inner mesh 66, mesh sleeve 38, and outer mesh 68 establishing an electric field between the inner mesh and the mesh outer mesh and between the mesh sleeve and the outer mesh. Further, the UV radiation from lamp 50 results in photo-emission of electrons from the inner mesh 66 such that this mesh acts as a cathode. These electrons are attracted toward the outer mesh (which therefore acts as an anode) but attach themselves to the dielectric body 30 along the way. The body retains the static charge owing to its high electric impedance. (Note that a dielectric body 30 fabricated of quartz fibres is particularly advantageous in this regard due the high electrical resistance of quartz). This effect enhances the electric field established in the body 30. Blower 20 draws contaminated air from intake 14, though intake dust filter 19, and expels it into the central cavity 34 of UV chamber 60. The pressurized air in the inner cavity 34 moves downstream from the inner cavity 34 through dielectric body 30 to the outer filters 40 and 42. In doing so, much of the biological material (such as bacteria and viruses) in the air becomes trapped in the electric fields set up between meshes 38, 66, and 68. Further, water vapor and ozone in the air is absorbed by the dielectric body 30. These materials are converted to OH both in the gas phase and on the dielectric fill. As the air passes through outer filters 40 and 42, residual biological material and chemicals are removed from the air. Both are destroyed by the wash of residual UV2 and by OH that is entrained in the air.

With lamp 50 activated, FIG. 3*a* graphically illustrates the intensity of UV1, UV2 and UV3 radiation as a function of radial distance in the lamp cross-section illustrated in FIG. 3. Turning to these figures, it will be seen inner cavity 34 of UV chamber 60 is flooded with UV1, UV2 and UV3 light (section 100) and the dielectric body 30 is flooded with (predominately) UV2 and UV3 light (section 102). A small amount of UV2 light passes through screen mesh sleeve 38 and into filters 40 and 42 (section 104). The UV reflective coatings of walls 24 and 32 as well as of housing 12 and inner mesh 66 enhance the intensity of UV radiation in the central cavity 34. The UV reflective coating on walls 24 and 32 and on the screen mesh sleeve 11 enhance the intensity of UV radiation in the dielectric body 30. The UV absorbing coatings of intake plenum 18 and exhaust plenum 62 help ensure that any UV light reaching these extremities of purifier are absorbed and do not leave the purifier (section 106).

The UV radiation produced by lamp 50 produces the following chemical reactions.

$$O_2 + UV1 \rightarrow O + O \qquad (1)$$

$$O_2 + O \rightarrow O_3 \qquad (2)$$

$$O_3 + UV1 \text{ or } UV2 \rightarrow O^* + O2 \qquad (3)$$

$$O^* + H_2O \rightarrow 2OH \qquad (4)$$

$$O^* + O_2 \rightarrow O_3 \qquad (5)$$

$$H_2O + UV1 \rightarrow OH + H \qquad (6)$$

$$O + O_2 \rightarrow O_3 \qquad (7)$$

As will be appreciated by those skilled in the art, these reactions have been simplified. In fact, other free radicals (such as H and $HO_2$) and compounds (such as $H_2O_2$) will play roles.

UV1 radiation produced by lamp 50 photo-dissociates oxygen ($O_2$) in the air resulting in the formation of ground state atomic oxygen (reaction (1)). This atomic oxygen is highly chemically reactive. A large portion of this atomic oxygen reacts with $O_2$ to form ozone ($O_3$: reaction (2)). Ozone may be further photo-dissociated by UV1 or UV2 to form excited atomic oxygen ($O^*$: reaction (3)). As will be appreciated by those skilled in the art, the optimum UV wavelength for dissociating ozone is about 250 nm. This excited atomic oxygen is even more chemically reactive than the oxygen formed in reaction (1) and rapidly attacks any water vapor present to form OH by reaction (4). The excited atomic oxygen can also be deactivated by oxygen ($O_2$) and nitrogen ($N_2$) in the air to form ground state atomic oxygen which then reacts with $O_2$ to reform ozone (reactions (5), (6) and (7)).

Atomic oxygen, ozone ($O_3$) and hydroxyl radicals (OH) will react with organic compounds and break them into oxidized fragments. However, OH removes most organic compounds at rates up to ten orders of magnitude faster than ozone. Further, ozone is a toxic gas. OH, on the other hand, is not a hazard because it is so chemically reactive that is cannot survive more than a few second in normal air. Thus, unlike ozone, it cannot accumulate.

In view of the forgoing it is desirable to create as much OH and a little ozone as possible. This means enhancing reactions (3) and (4) relative to reactions (5) to (7). This is achieved by dielectric body 30 which traps ozone, thereby increasing the rate of its photo-dissociation by reaction (3), and which traps water vapor and ozone for use in reaction (4).

A highly porous dielectric body can absorb water or ozone to up to about 30% of its weight. The high absorbency and higher density of the dielectric body 30 relative to air results in an enhancement of the volume density of water and ozone of about three orders of magnitude. The dielectric body will absorb water vapor even when relative humidity is low making it unnecessary to add water vapor to the system.

Because UV1 is primarily or entirely contained within inner cavity 34 of UV chamber 60, it will be apparent that atomic oxygen is primarily formed in the inner cavity (reaction 1). Ozone will therefore be formed (by reaction 2) in the inner cavity and in the dielectric body. Because the body 30 is primarily radiated with UV2, little ground level atomic oxygen (O)—which generates ozone—will be formed in the body. Instead, the UV2 irradiating the body will primarily photo-dissociate the ozone trapped by the body resulting in excited atomic oxygen (reaction (3)). Given the high concentration of water vapor in the body 30 and the presence of excited atomic oxygen there, OH (by reaction (4)) is formed primarily in the dielectric body.

If a suitable dielectric material is added to the inner cavity 34, or if a porous UV1, UV2 and UV3 transmitting dielectric is coated onto the lamp walls, the production of OH by reaction (6) will increase relative to reactions (1) and (2). This enhancement results from the high absorption of $H_2O$ relative to $O_2$ onto the surfaces of many dielectrics (e.g. silica gel or aluminum oxide). This effect can be useful in embodiments in which it is desirable to further minimize ozone production.

Figure 4:
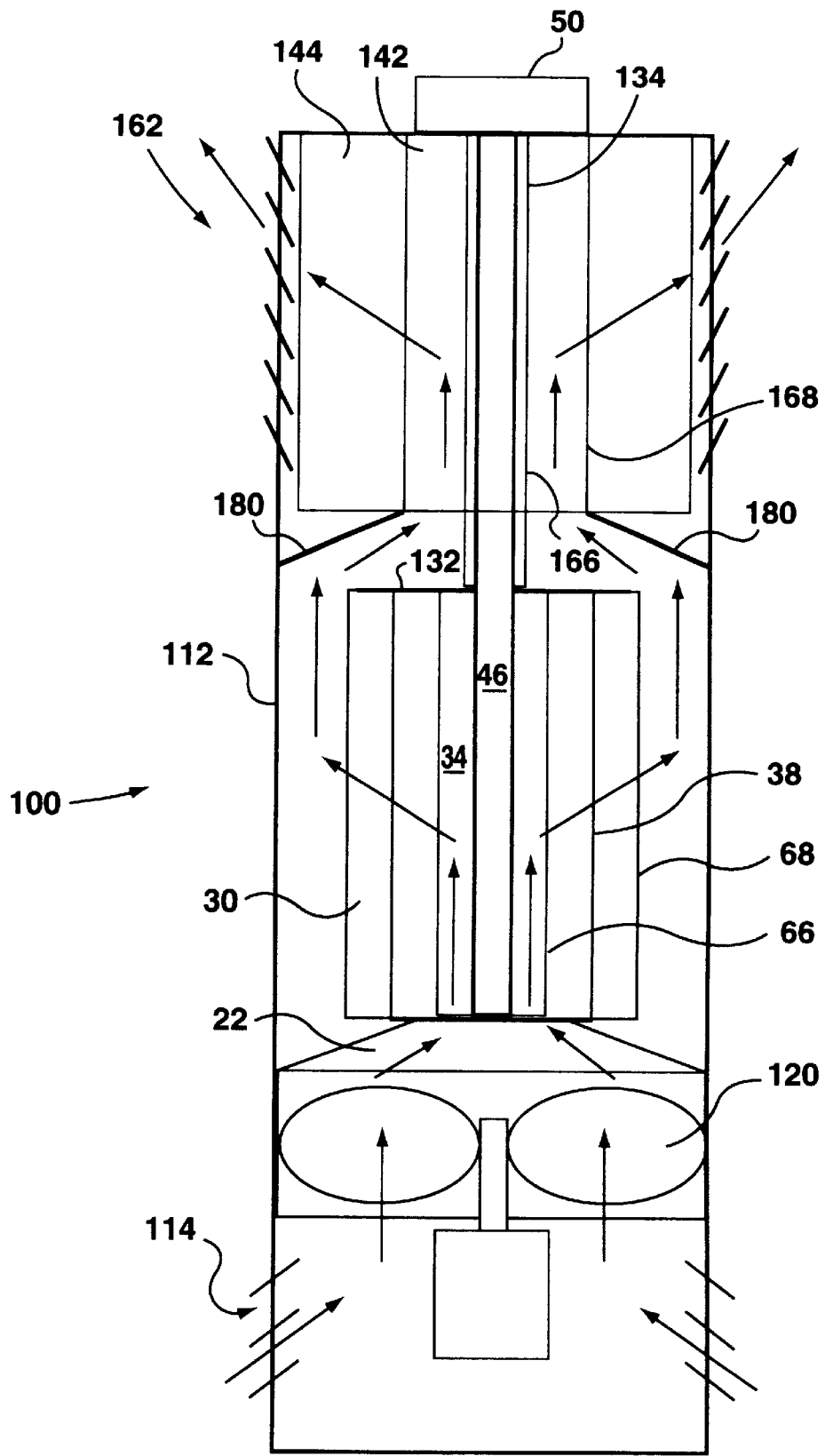
FIG. 4 is a schematic side view of an air purifier made in accordance with another embodiment of this invention.

For example, by applying a pure silica gel coating 90 (FIG. 1) which is a few millimeters thick to the light emitting tube 46 of the lamp 50 of FIG. 1 or 4, the $H_2O$ present in the coating will absorb all the UV1, converting the $H_2O$ directly to OH. This will reduce the ozone production but will not block UV2 and UV3 radiation from the lamp.

As noted, the OH and atomic oxygen will fragment (oxidize) organic compounds thus destroying bacteria and viruses in the air. This will also result in fragmentation of other volatile organic compounds and organic pollutants which may be in the air, thereby reducing their concentration.

Organic compounds may stick to the dielectric body 30. However, OH will rapidly attack these surface contaminants thereby fragmenting these materials. If the fragmented materials continue to stick, they continue to be fragmented until, in many cases, water vapor and carbon dioxide results. Carbon dioxide ($CO_2$) is not absorbed by zeolite or charcoal. Thus, where the outer chemically absorbent filter 42 is fabricated of such materials, $CO_2$ will float away and out of the purifier. Since the concentrations of volatile organic compounds are small (less than a part per million) compared to the ambient concentration of $CO_2$ (about 300 parts per million), any increase in $CO_2$ caused by the oxidation of volatile organic compounds by the purifier is negligible compared to other sources and will pose no health risk.

The UV light itself will also act to sterilize biological materials in the intake air. This is particularly so in respect of material trapped by the electric field in the body 30 or trapped in outer filter 42 in view of the increased time during which such biological materials is exposed to the UV light.

Ozone reaching the outer filter 42 is readily absorbed. While it is absorbed on the filter it will be broken down by the (small) amount of UV (UV2) radiation reaching outer filter 42 and will form OH. This reaction can be facilitated by adding a catalytic mesh (with a material such as $TiO_2$) to these filters.

Screen mesh 38 could be replaced with a porous wall formed of fused UV reflecting grains having a diameter approximating that of the UV2 radiation. These UV reflecting grains could, for example, be spheres of aluminum, high purity silica, or grains of barium sulfate. It might also be fabricated out of aerogel matrices with the desired average pore sizes.

While lamp 50 is described as emitting UV1, UV2 and UV3 radiation, air will still be purified by the purifier 10 (albeit not as efficiently or completely) if the lamp emitted solely UV1 or UV2 radiation. Further, two or three lamps could be provided, one which emits UV1 radiation into the airflow path upstream of the dielectric body, a second one which emits UV2 light into the dielectric body itself and a third one which emits UV3 radiation for use in the outer filters and outer wall.

FIG. 4 illustrates an air purifier 100 in accordance with another embodiment of this invention. Turning to FIG. 4, wherein like parts have like reference numerals, housing 112 of purifier 100 is tubular. Air inlets 114 in one end of the housing feed to blower 120. An outlet plenum 22 extends between the exhaust of the blower and the central cavity formed by the annular dielectric body 30. An annular plate wall 132 abuts the end of the dielectric body 30 remote from plenum 22. Baffles 180 extend between housing 112 and an end of annular particulate filter 142. A chemically absorbent outer filter 144 extends between particulate filter 142 and air exhaust 162. Lamp 50 through the annulus formed by the particulate filter 140 and the annulus formed by dielectric body 30. As well as the inner and outer annular wire mesh 66, 68 associated with the dielectric body, there is an inner and outer wire mesh 166, 168 associated with the filters 140, 142. Like meshes 66, 68, meshes 166, 168 are polarised with a voltage source (not shown). With purifier 100, when blower 120 is activated, air flows out from the blower into dielectric body 30, then out from the body to between body 30 and the wall of housing 112. Air then passes into particulate filter 40, then through outer filter 42 and out exhaust 162. Unlike purifier 10 (FIG. 1), there are no filters surrounding dielectric body 30. Instead, filters 140, 142, while concentric with lamp 50, are separate from the body 30. With this arrangement, UV light falls directly on the particulate and chemical filters. Appropriate screen meshes could be added to enhance UV2 in the cavity 134 inside the two filters 140, 142. In addition, photoelectric effect mesh electrodes 166, 168, if added to filters 40 and 42, enhance their effectiveness. Instead of a mesh electrode, one method of producing a cathode might entail a coating of cesium iodide or similar material on an inner face of one of the filters. This coating would absorb wavelengths shorter than 185 NM and produce photo-electrons at such wavelengths. It would also be transparent at wavelengths longer than 200 NM. Thus, the cathode would inhibit the emission of UV1 past filters 140, 142 by blocking the ozone producing UV but still allow UV2 and UV3 to be emitted which would sterilize the filters 140, 142 and aid photochemical processes.

A basic purifier in accordance with this invention would comprise a source of UV which irradiates a suitable dielectric body interposed in the airflow path of the purifier. The effectiveness of the purifier is enhanced by the addition of a cathode and anode to attract and trap charged particles for UV irradiation. Further improvement in efficiency is obtained with the addition of the each of the other features described, such as the described filters and coatings.

Other modifications will be apparent to those skilled in the art and, therefore, the ambit of the invention is set out in the claims herefollowing.

What is claimed is:

1. An air purifier comprising:

an air flow path;

a dielectric body which is porous to air and transmissive to ultraviolet light interposed across said air flow path; and a source of ultraviolet light arranged for emitting UV1 light being light being below approximately 185 nm in wavelength light, and UV2 light, being light between 185 nm and 300 nm in wavelength, such that said UV1 light is present in said air flow path upstream of said dielectric body and said UV2 Light is present in said dielectric body at a higher intensity than any UV1 light present in said dielectric body.

2. The air purifier of claim 1 wherein said dielectric body absorbs UV1 light more strongly than UV2 light.

3. The air purifier of claim 1 wherein said dielectric body comprises silica.

4. The air purifier of claim 1 wherein said dielectric body comprises silica gel.

5. The air purifier of claim 1 wherein said dielectric body comprises silica granules.

6. The air purifier of claim 1 wherein said dielectric body comprises quartz fibers.

7. The air purifier of claim 6 wherein said quartz fibers are coated with a silica coating.

8. The air purifier of claim 1 wherein said dielectric material comprises alumina fibers.

9. The air purifier of claim 1 wherein said dielectric body comprises a material which strongly attaches to water and ozone.

10. The air purifier of claim 1 wherein said dielectric body has a pore size sufficiently large to admit ozone and water molecules and sufficiently small to enhance attachment of water and ozone to said dielectric body.

11. The air purifier of claim 1 further comprising a mesh surrounding said dielectric body having a mesh size at least an order of magnitude less than a longest wavelength of said UV2 light.

12. The air purifier of claim 1 wherein said source of ultraviolet light also emits UV3 light, being light above about 300 nm in wavelength.

13. The air purifier of claim 12 further comprising a filter in said airflow path downstream of said dielectric body, said filter being porous to air, said filter arranged for trapping biological fragments.

14. The air purifier of claim 13 wherein at least one of said dielectric body and said filter has a photocatalytic material.

15. The air purifier of claim 14 wherein said photocatalytic material is $TiO_2$.

16. The air purifier of claim 1 wherein said dielectric body is annular and said source of ultraviolet light emits within a central cavity of said dielectric body.

17. The air purifier of claim 16 wherein said source of ultraviolet light is a lamp extending within said cavity.

18. The air purifier of claim 17 wherein said lamp has a silica gel coating.

19. The air purifier of claim 16 wherein said central cavity is sized so that a preponderance of said UV1 light is absorbed in said central cavity.

20. The air purifier of claim 16 wherein said central cavity is arranged to absorb a preponderance of said UV1 light.

21. The air purifier of claim 1 wherein said source of ultraviolet tight emits UV1 and UV2 light at a stand-off from said dielectric.

22. An air purifier comprising:

an air flow path;

a dielectric body which is porous to air and transmissive to ultraviolet light interposed across said air flow path;

a source of ultraviolet light for emitting ultraviolet light such that ultraviolet light is present in said dielectric body; and.

an anode and a cathode in said dielectric body surrounding said source of ultraviolet light.

23. The air purifier of claim 22 wherein said cathode is more proximate to said source of ultraviolet radiation than said anode.

24. The air purifier of claim 23 wherein said cathode has a coating which is highly reflective of ultraviolet light.

25. The air purifier of claim 24 wherein said coating comprises rhodium coated aluminum.

26. A method of air purification comprising:

passing contaminated air through a dielectric body which is porous to air and transmissive of ultraviolet ("UV") radiation;

irradiating said dielectric body such that the intensity of radiation between 185 nm and 300 nm in wavelength in said dielectric body is greater than the intensity of any radiation below approximately 185 nm in wavelength in said dielectric body; and UV irradiating said airflow path upstream of said dielectric body with at least radiation below approximately 185 nm in wavelength.

* * * * *